(12) United States Patent
Choi et al.

(10) Patent No.: US 7,361,762 B2
(45) Date of Patent: Apr. 22, 2008

(54) PROCESS FOR PREPARING ACID SALTS OF GEMIFLOXACIN

(75) Inventors: Hoon Choi, Taejeon (KR); Sang-Chul Choi, Taejeon (KR); Do-Hyun Nam, Taejeon (KR); Bo-Seung Choi, Taejeon (KR)

(73) Assignee: LG Life Sciences Ltd., Seoul (KR)

( * ) Notice: Subject to any disclaimer, the term of this patent is extended or adjusted under 35 U.S.C. 154(b) by 98 days.

(21) Appl. No.: 10/510,514

(22) PCT Filed: Apr. 4, 2003

(86) PCT No.: PCT/KR03/00683

§ 371 (c)(1),
(2), (4) Date: Nov. 1, 2004

(87) PCT Pub. No.: WO03/087100

PCT Pub. Date: Oct. 23, 2003

(65) Prior Publication Data

US 2005/0148622 A1    Jul. 7, 2005

(30) Foreign Application Priority Data

Apr. 8, 2002    (KR) .................. 10-2002-0018847

(51) Int. Cl.
*C07D 221/02* (2006.01)
(52) U.S. Cl. ..................................... 546/112
(58) Field of Classification Search ................ 546/112, 546/123
See application file for complete search history.

(56) References Cited

U.S. PATENT DOCUMENTS

| 5,633,262 | A | 5/1997 | Hong et al. |
| 5,776,944 | A | 7/1998 | Hong et al. |
| 5,869,670 | A | * 2/1999 | Hong et al. ............... 546/123 |
| 5,962,468 | A | 10/1999 | Hong et al. |
| 6,307,059 | B1 | 10/2001 | Chang et al. |

FOREIGN PATENT DOCUMENTS

| EP | 0 058 614 | A | 8/1982 |
| EP | 0 266 576 | A3 | 5/1988 |
| EP | 0 183 129 | B1 | 8/1989 |
| EP | 0 326 891 | A3 | 8/1989 |
| EP | 0 541 086 | A1 | 5/1993 |
| EP | 0 688 772 | A1 | 12/1995 |
| EP | 0 805 156 | A | 11/1997 |
| EP | 0 688 772 | B1 | 5/1999 |
| JP | 1-100165 | A | 4/1989 |
| JP | 3-56479 | A | 3/1991 |
| JP | 6-73056 | A | 3/1994 |
| WO | WO-91/02526 | A1 | 3/1991 |
| WO | WO-92/10191 | A1 | 6/1992 |
| WO | WO-96/39406 | A1 | 12/1996 |
| WO | WO-97/07098 | A1 | 2/1997 |
| WO | WO-97/36874 | A1 | 10/1997 |
| WO | WO-98/42705 | A1 | 10/1998 |
| WO | WO-99/44991 | A1 | 9/1999 |
| WO | WO-99/61420 | A1 | 12/1999 |
| WO | WO-00/17199 | A1 | 3/2000 |
| WO | WO-01/00209 | A1 | 1/2001 |
| WO | WO-01/15695 | A1 | 3/2001 |
| WO | WO-01/17961 | A2 | 3/2001 |
| WO | WO-01/18002 | A1 | 3/2001 |
| WO | WO-01/21176 | A1 | 3/2001 |
| WO | WO-01/68649 | A1 | 9/2001 |
| WO | WO-02/18336 | A1 | 3/2002 |

OTHER PUBLICATIONS

Alex R. Khomutov, Alexander S. Shvetsonv, Jouko J. Vesalainen and Anatoly M. Kritzyn, Novel acid-free cleavage of N-(2-hyroxyaryliene) protected amines, Tetrahedron Letters 42:2887-2889 (2001).*
Chang Yong Hong, Young Kwan Kim, Yong Hee Lee, and Jin Hwan Kwak, Methyloxime-Substituted Aminopyrrolidine: A new Surrogate for 7-Basic Group of Quinolone, Bioorganic & Medicinal chemistry Letters 8:221-226 (1998).*
P. Bey and J.P. Vevert, Synthesis of alpha-Alkyl and alpha-Functionalized Methyl-alpha-Amino Acids, Tetrahedron Letters 17:1455-1458 (1977).*
Martin J. O'Donnell, James M. Boniece adn Samuel E. Earp, The Synthesis of Amino Acids by Phase-Transfer Reactions, Tetrahedron Letters 30:2641-2644 (1978).*
Khomutov et al., Novel Acid-Free Cleavage of N-(2-hydroxyarylidiene) protected amines, Tetrahedron Lett., 42:2887-2889 (2001).*
A. Graul et al., "Fluoronaphthyridinecarboxylic Acid Antibacterial; In Drugs of the Future", (1998), 23(11), 1199-1204.

* cited by examiner

*Primary Examiner*—D. Margaret Seaman
(74) *Attorney, Agent, or Firm*—Birch, Stewart, Kolasch & Birch, LLP

(57) ABSTRACT

The present invention relates to a process for preparing acid salts of Gemifloxacin, a quinolone type antibiotic agent having potent antimicrobial activity. The process according to the present invention can provide advantages such as simplicity of process, improvement of productivity and improvement of yield, and the like by reducing conventional three-step process to two-step process.

14 Claims, No Drawings

PROCESS FOR PREPARING ACID SALTS OF GEMIFLOXACIN

TECHNICAL FIELD

This invention relates to a novel process for preparing acid salts of quinolone carboxylic acid, that is, 7-(3-aminomethyl-4-methoxyiminopyrrolidin-1-yl)-1-cyclopropyl-6-fluoro-4-oxo-1,4-dihydro-1,8-naphthyridine-3-carboxylic acid (hereinafter referred to Gemifloxacin), having a potent antimicrobial activity and represented by the following formula 1:

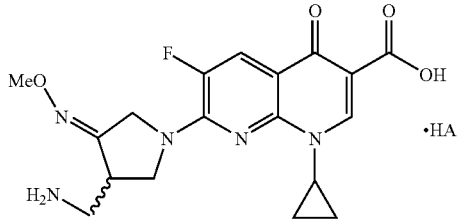

wherein,

Me represents methyl,

HA is an organic acid or an inorganic acid.

BACKGROUND ART

Said Gemifloxacin and its salts are compounds disclosed in Korean Patent No. 131999 to the present inventors (Korean Patent Application No. 94-13604, foreign patents corresponding to this patent: EP 688722 A1, JP Patent No. 41050/1996, Russian Patent No. 2120940, Canadian Patent No. 2151890, Chinese Patent No. 1114959, and U.S. Pat. Nos. 5,962,468, 5,869,670, 5,840,916, 5,776,944, 5,698,570 and 5,633,262). These compounds have a potent antimicrobial activity, and moreover can be effectively used as agents for treating human being or animals infected by bacteria.

The present inventors had prepared said acid salts of Gemifloxacin by a three-step reaction process, that is, a synthesis process through a coupling reaction, a salt formation, and a recrystallization, as represented by the following reaction scheme 1:

(Reaction scheme 1)

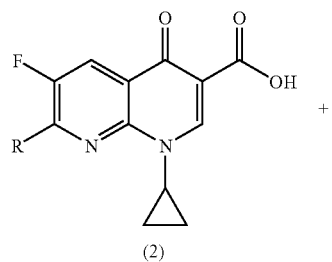

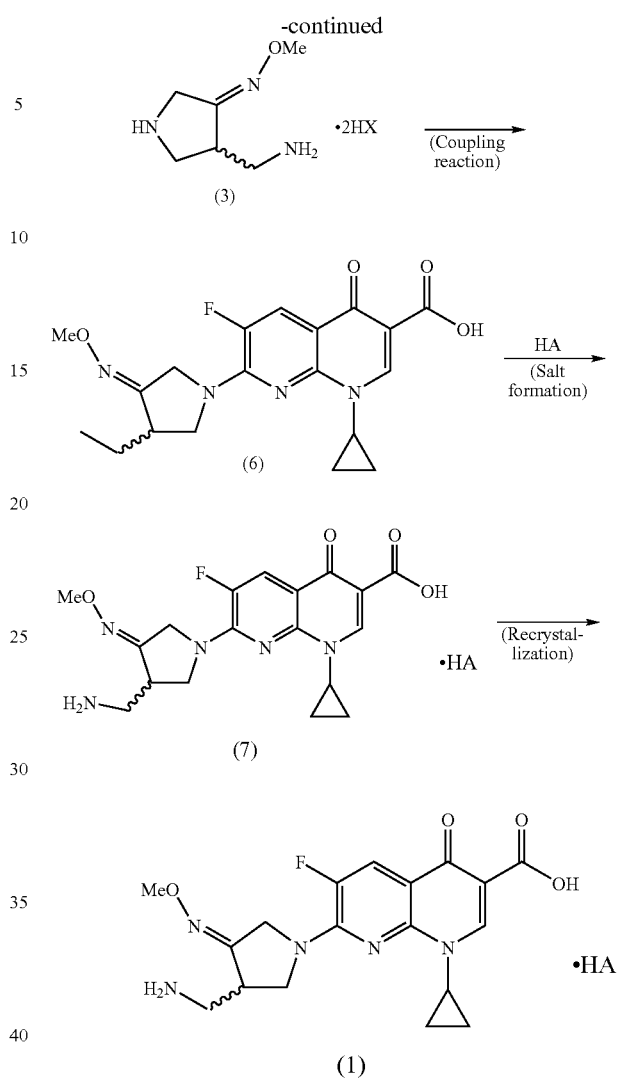

wherein,

Me represents methyl,

R represents Cl, F, Br, I, methanesulfonyl, or paratoluenesulfonyl,

HX represents hydrochloric acid, hydrobromic acid, hydroiodic acid, trifluoroacetic acid, methanesulfonic acid, paratolunesulfonic acid, or sulfueric acid, HA is an organic acid or an inorganic acid.

As shown in the above reaction scheme 1, the compound (1) is prepared through three-step reaction process, that is, a coupling reaction, a salt formation and a recrystallization. The reason why the three-step reaction process is carried out is because the compound (8) as impurity is formed in an amount of approximately 6-12% by a side-reaction under the coupling reaction and the compound (8) is remained in the compound (6) in an amount of approximately 0.3 to 1.0%. To remove the resulting impurity through the coupling reaction at 0.1% or less, the second step, that is a salt formation process, had to be carried out. Finally, the organic solvent used in the salt formation process had to be removed from the step of recrystallization.

Through the three step process, an acid salt of Gemifloxacin (1) as a raw medicine having high purity was prepared in about 65% of total yield. Since the resulting impurity (8) from the coupling reaction of the above process was difficult to be removed, the salt formation and recrystallization steps for removing the impurity had to be carried out.

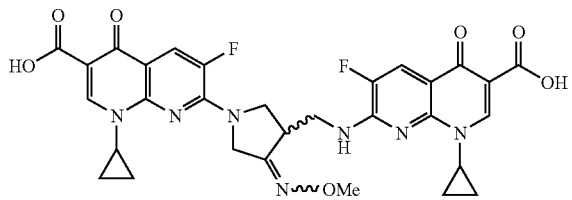

8

DISCLOSURE OF INVENTION

The present inventors have conducted intensive studies in view of reducing the above three-step reaction process to a two-step process. As a result, they have found that the preparing process comprising two steps below have several advantages, such as simplicity of the preparation process, improvement of productivity and increase of yield. Therefore, they have completed the present invention.

The present invention provides a process for preparing acid salts of Gemifloxacin represented by formula 1, which comprises the steps of a) adding a compound of formula 5 to naphthyridine carboxylic acid of formula 2 and 3-aminomethyl-4-methoxy-iminopyrrolidine salt of formula 3 in water, an organic solvent or a mixed solvent thereof in the presence of an organic base to carry out a coupling reaction, and b) adding an acid of formula HA to the resulting compound of formula 4 in water, an organic solvent or a mixed solvent thereof to carry out deprotection and salt formation reactions at the same time:

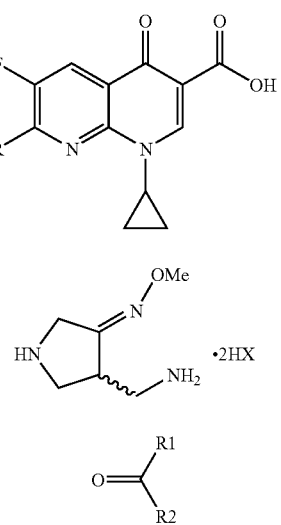

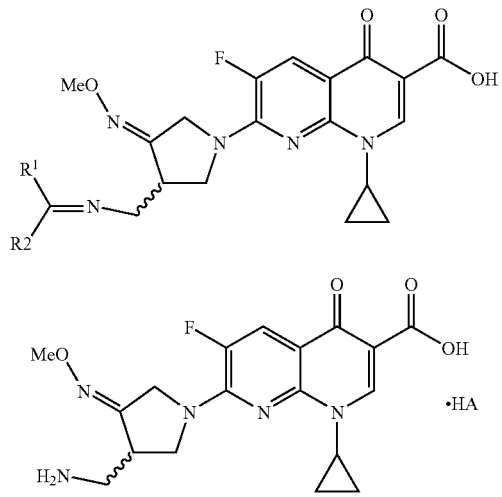

wherein,
R represents Cl, F, Br, I, methanesulfonyl or paratoluenesulfonyl,
Me represents methyl,
HX represents hydrochloric acid, hydrobromic acid, hydroiodic acid, trifluoroacetic acid, methanesulfonic acid, paratolunesulfonic acid, or sulfuric acid,
R1 and R2 independently of each other represent hydrogen, a straight or branched, saturated or unsaturated $C_1$~$C_6$ alkyl group, a saturated or unsaturated $C_3$~$C_6$ cycloalkyl group, or an aromatic group which is unsubstituted or substituted by $C_1$~$C_6$ alkyl, $C_1$~$C_6$ alkoxy, hydroxy, cyano or halogen, or
R1 and R2 together with a carbonyl group to which they are bonded form a ring, and
HA is an organic acid or an inorganic acid.

BEST MODE FOR CARRYING OUT THE INVENTION

The preparation process according to the present invention is described in detail as the following reaction scheme 2:

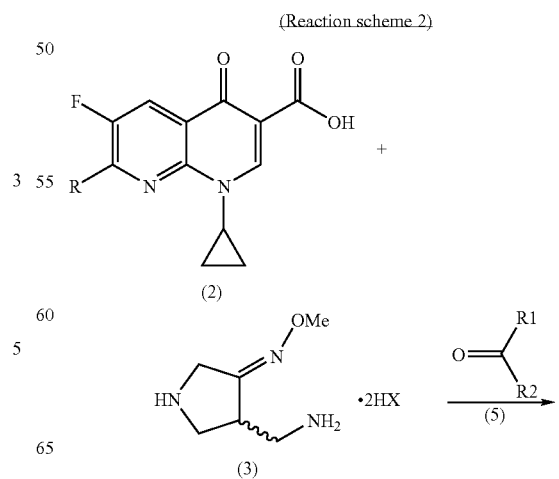

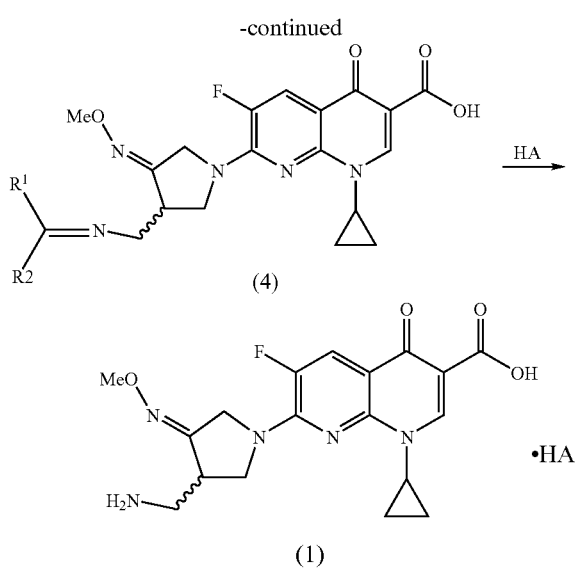

(4)

(1)

wherein,
Me, R, R1, R2, HX and HA are as defined above.

As shown in the above reaction scheme 2, to reduce the steps of a salt formation and a recrystallization to one step by preventing production of impurity (8), the compound (5) having a carbonyl group may be added to the compound (3) under a coupling reaction to protect a primary amino group in the compound (3) with the compound (5). Due to this protection, production of by-product (8) may be remarkably prevented in an amount of 0.1% or less. The resultant compound (4), which is prepared from the above process in a yield of about 90% or more, is treated with an acid of formula HA to carry out deprotection and salt formation reactions by one step. By means of the above procedure omitting the step of the recrystallization reaction, an acid salt of Gemifloxacin of the compound (1) is produced in a yield of 90% or more, and the steps of the preparation process are simplified. In accordance with such a simplification of the preparation process, the following several effects can be obtained: reducing production time, improving productivity and increasing yield.

The process according to the present invention is explained as an example in detail as below:

First, the synthesis process of the compound (4) (step a) comprises dissolving the compound (3), the compound (5) and an organic base, for example triethylamine in a reaction solvent, for example a mixed solvent of acetonitrile with water, and adding the compound (2) thereto, and then reacting the resulting mixture. The reaction conditions of this reaction are as follows:

1) As a reaction solvent, water, an organic solvent, such as acetonitrile, tetrahydrofuran (THF), methanol, and ethanol, or a mixed solvent of an organic solvent with water may be used. Preferably, a mixed solvent of acetonitrile with water is advantageous in view of purity and yield.
2) As a compound (5), ketone or aldehyde compound, such as formaldehyde, acetone, benzaldehyde, 1-butylaldehyde, and the like, may be used. Preferably, benzaldehyde derivative, such as benzaldehyde, 2-hydroxybenzaldehyde, 2-chlorobenzaldehyde and the like is advantageous in view of purity and yield. Particularly, benzaldehyde is the most advantageous in view of cost and stability. It is preferred that benzaldehye is used in an amount of the molar amount equal to or more than the molar amount of the compound (2).
3) A reaction temperature may be applied thereto in the wide range of 0° C. to 80° C. However, the most preferred temperature is in the range of 20~30° C. in view of reaction rate, yield and purity.
4) As an organic base, triethylamine, trimethylamine, diisopropylethylamine, DBU (1,8-diazabicyclo[5.4.0]undec-7-ene), DBN (1,5-diazabicyclo[4.3.0]non-5-one), as well as a number of the other bases may be used. The most suitable base is triethylamine in view of cost and yield. The amount thereof is used in 3 or more molar amount relative to the compound (2).

By carrying out the above reaction process, the compound (4) having high purity may be produced in high yield (more than 90%).

Second, the process (step b) for preparing the compound (1) from the compound (4) comprises dissolving the compound (4) in a reaction solvent, for example, a mixed solvent of isopropanol with water, heating the resultant mixture, adding an acid of formula HA, for example, methansulfonic acid, thereto to carry out deprotection and salt formation reactions at the same time, and then cooling the reaction material to prepare the compound (1) without the recrystallization step. The reaction conditions of this reaction are as follows:

1) As a reaction solvent, water, alcohol, such as isopropanol, THF, methanol, ethanol, butanol and the like, or a mixed solvent of alcohol with water may be used. Preferably, a mixed solvent of isopropanol with water is advantageous in view of purity and yield.
2) As an acid, a number of acids representing HA, such a hydrochloric acid, methanesulfonic acid, sulfuric acid, phosphoric acid, acetic acid, citric acid, tartaric acid, perhydrochioric acid, picric acid, (+)-camphor sulfonic acid and the like may be used. Particularly, methansulfonic acid is the most suitable. It is preferred to use the acid of formula HA in the amount of 80 mol % to 120 mol % relative to the compound of formula (4).
3) A reaction temperature may be applied thereto in the wide range of 0° C. to 100° C. However, the reaction temperature of 40~50° C. on adding an acid and the reaction temperature of 0~20° C. after adding the acid are preferred, in view of reaction rate of the final compound (1), yield and purity.

By carrying out the above reaction process, the compound (4) having high purity may be produced in high yield (more than 90%).

As described hereinbefore, if a novel synthesis process of two steps is used, the improved effect such as simplicity of the preparation process, increase of yield (from about 65% to at least 80%), improvement of productivity, decrease of manufacturing costs and the like can be achieved by reducing three steps of conventional synthesis process to two steps. Specifically, it has an advantage that this process may be applied to quinolone type antibiotics having a similar structure to that of Gemifloxacin.

Therefore, the present invention provides an outstandingly improved technique over the prior art.

The present invention is explained in detail by means of the following examples, which are not intended to limit the scope of the invention.

EXAMPLES

Example 1

Preparation of 7-(3-benzylidineaminomethyl-4-methoxyimino-1-pyrrolidinyl)-1-cyclopropyl-6-fluoro-1,4-dihydro-4-oxo-1,8-naphthyridine-3-carboxylic acid

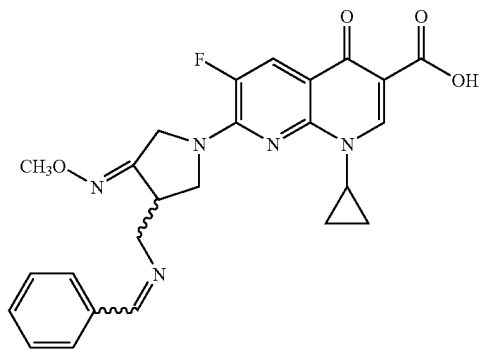

Acetonitrile (1900 ml), 3-aminomethyl-4-methoxyiminopyrrolidine dimethanesulfonate (248.0 g) and water (100 ml) were in turn introduced into a reaction vessel and cooled to 0~5° C. Benzaldehyde (97.6 g) and triethylamine (229.1 g) were in turn added to the reaction mixture. After stirring the mixture for 0.5 h, 7-chloro-1-cyclopropyl-6-fluoro-1,4-dihydro-4-oxo-1,8-naphthyridine-3-carboxylic acid (200.0 g) was introduced thereto. The resultant reaction mixture was slowly heated to room temperature, while stirring it. Then, the reaction was carried out by stirring the reaction mixture for about 3 h at room temperature. The reaction material, which was formed in the form of a dispersion solution upon producing the title compound, was filtered, washed with water and acetonitrile, and then dried to prepare 320.3 g of the title compound (Yield: 94.8%).

$^1$H NMR (δ, CDCl$_3$): 8.66 (s, 1H), 8.32 (s, 1H), 7.98 (d, J=12.4 Hz, 1H), 7.60 (d, J=7.0 Hz, 2H), 7.37 (t, J=7.4 Hz, 1H), 7.31 (t, J=7.4 Hz, 2H), 4.58 (s, 2H), 4.21~4.15 (m, 2H), 4.00 (m, 1H), 3.93 (s, 3H), 3.83 (m, 1H), 3.56 (m, 1H), 3.40 (m, 1H), 1.21 (m, 2H), 1.00 (m, 2H) Mass (FAB): 478 (M+H)

Example 2

Preparation of 7-[3-(2-chlorobenzylidine)aminomethyl-4-methoxyimino-1-pyrrolidinyl]-1-cyclopropyl-6-fluoro-1,4-dihydro-4-oxo-1,8-naphtyridine-3-carboxylic acid

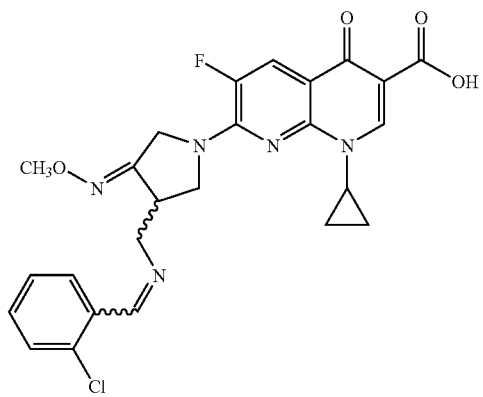

Acetonitrile (100 ml), 3-aminomethyl-4-methoxyiminopyrrolidine dimethanesulfonate (12.5 g), 2-chlorobenzaldehyde (10.0 g) and triethylamine (12.2 g) were in turn introduced into a reaction vessel at room temperature. After stirring the mixture for about 0.5 h, 7-chloro-1-cyclopropyl-6-fluoro-1,4-dihydro-4-oxo-1,8-naphthyridine-3-carboxylic acid (10.0 g) was introduced thereto. The resultant reaction mixture was stirred for about 15 h at room temperature, cooled to 0~5° C., and stirred for about 3 h. The title compound in the form of solid was filtered, washed with acetonitrile, and dried to prepare 16.3 g of the title compound (Yield: 90.0%).

$^1$H NMR (δ, CDCl$_3$): 8.74 (s, 1H), 8.66 (s, 1H), 7.96 (d, J=12.4 Hz, 1H), 7.84 (d, J=7.3 Hz, 1H), 7.29 (m, 2H), 7.16 (m, 1H), 4.59 (bs, 2H), 4.18 (m, 2H), 4.02 (m, 1H), 3.94 (s, 3H), 3.93 (m, 1H), 3.59 (m, 1H), 3.42 (m, 1H), 1.22 (m, 2H), 1.01 (m, 2H) Mass (FAB): 512 (M+H)

Example 3

Preparation of 7-[3-(2-hydroxybenzylidine)aminomethyl-4-methoxyimino-1-pyrrolidinyl]-1-cyclopropyl-6-fluoro-1,4-dihydro-4-oxo-1,8-naphthyridine-3-carboxylic acid

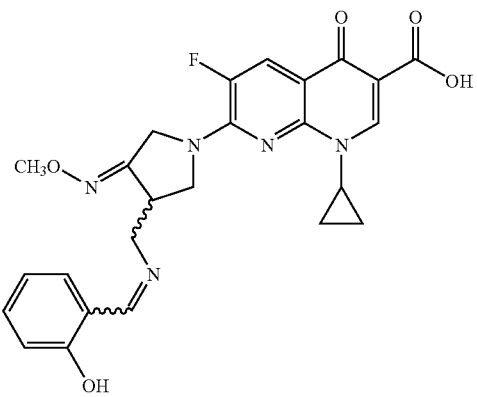

Acetonitrile (100 ml), 3-aminomethyl-4-methoxyiminopyrrolidine dimethanesulfonate (12.5 g), 2-hydroxybenzaldehyde (8.6 g) and triethylamine (12.2 g) were in turn introduced into a reaction vessel at room temperature. After stirring the mixture for about 0.5 h, 7-chloro-1-cyclopropyl-6-fluoro-1,4-dihydro-4-oxo-1,8-naphthyridine-3-carboxylic acid (10.0 g) was introduced thereto. The resultant reaction mixture was stirred for about 15 h at room temperature, cooled to 0~5° C., and stirred for about 3 h. The title compound in the form of solid was filtered, washed with acetonitrile, and dried to prepare 16.0 g of the title compound (Yield: 91.8%).

$^1$H NMR (δ, CDCl$_3$): 8.68 (s, 1H), 8.42 (s, 1H), 8.01 (d, J=12.4 Hz, 1H), 7.30~7.20 (m, 3H), 6.90~6.82 (m, 2H), 4.68~4.53 (m, 2H), 4.32~4.24 (m, 1H), 4.06 (dd, J1=11.9 Hz, J2=5.5 Hz, 1H), 4.02~3.85 (m, 3H), 3.95 (s, 3H), 3.60 (m, 1H), 3.40 (m, 1H), 1.29~1.21 (m, 2H), 1.07~1.00 (m, 2H) Mass (FAB): 494 (M+H)

Example 4

Preparation of 7-[3-(4-cyanobenzylidine)aminomethyl-4-methoxyimino-1-pyrrolidinyl]-1-cyclopropyl-6-fluoro-1,4-dihydro-4-oxo-1,8-naphthyridine-3-carboxylic acid

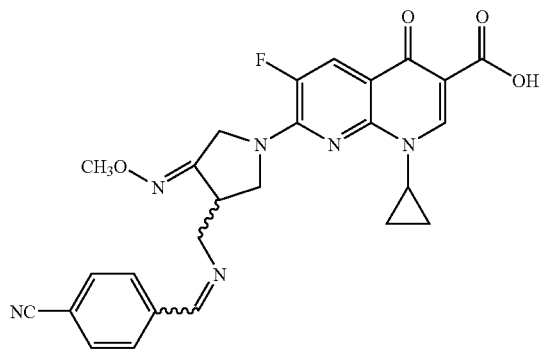

In accordance with the procedure and scale as described in Examples 2 and 3, 14.6 g of the title compound was prepared by using 4-cyanobenzalehyde (9.3 g) (Yield: 82.2%).

$^1$H NMR (δ, CDCl$_3$): 8.66 (s, 1H), 8.40 (s, 1H), 7.99 (d, J=12.4 Hz, 1H), 7.80 (d, 3=8.3 Hz, 2H), 7.67 (d, J=8.3 Hz, 2H), 4.59 (m, 2H), 4.30 (m, 1H), 4.08 (m, 2H), 3.92 (s, 3H), 3.90 (m, 1H), 3.61 (m, 1H), 3.45 (m, 1H), 1.24 (m, 2H), 1.05 (m, 2H) Mass (FAB): 503 (M+H)

Example 5

Preparation of 7-[3-(4-methoxybenzylidine)aminomethyl-4-methoxylimino-1-pyrrolidinyl]-1-cyclopropyl-6-fluoro-1,4-dihydro-4-oxo-1,8-naphthyridine-3-carboxylic acid

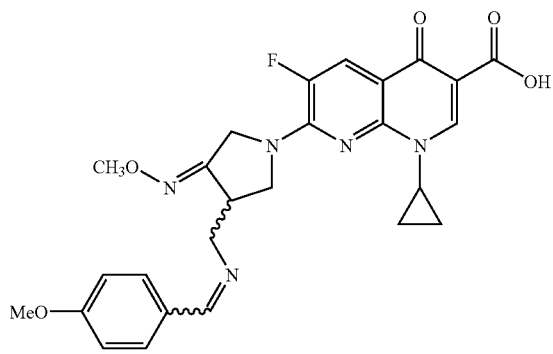

In accordance with the procedure and scale as described in Examples 2 and 3, 14.4 g of the title compound was prepared by using 4-methoxybenzaldehyde (9.6 g) (Yield: 80.2%).

$^1$H NMR (δ, CDCl$_3$): 8.66 (s, 1H), 8.22 (s, 1H), 7.96 (d, J=12.4 Hz, 1H), 7.52 (d, J=8.7 Hz, 2H), 6.79 (d, J=8.3 Hz, 2H), 4.59 (m, 2H), 4.16 (bs, 2H), 3.93 (s, 3H), 3.92 (m, 1H), 3.83 (m, 1H), 3.79 (s, 3H), 3.56 (m, 1H), 3.38 (m, 1H), 1.22 (m, 2H), 1.00 (m, 2H) Mass (FAB): 508 (M+H)

Example 6

Preparation of 7-[3-(1-naphthylidine)aminomethyl-4-methoxyimino-1-pyrrolidinyl]-1-cyclopropyl-6-fluoro-1,4-dihydro-4-oxo-1,8-naphthyridine-3-carboxylic acid

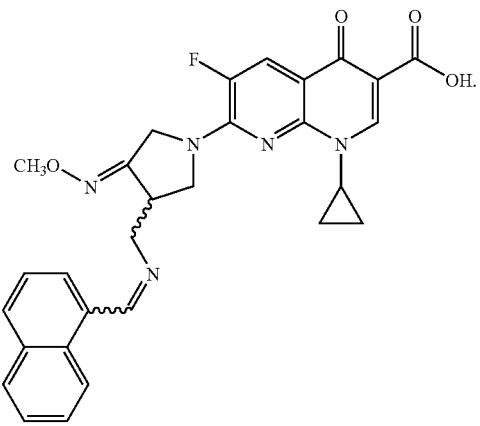

Acetonitrile (100 ml), 3-aminomethyl-4-methoxyiminopyrrolydine dimethanesulfonate (12.5 g) and 1-naphthaldehyde (11.1 g) were in turn introduced into a reaction vessel at room temperature and cooled to 0~5° C. Triethylamine (12.2 g) was dropwise added to the reaction mixture. After stirring the mixture for about 0.5 h, the reaction mixture was diluted by adding ethanol (30 ml). 7-Chloro-1-cyclopropyl-6-fluoro-1,4-dihydro-4-oxo-1,8-naphthyridine-3-carboxylic acid (10.0 g) was introduced to the reaction mixture. After raising slowly the reaction temperature to room temperature, the reaction mixture was stirred for about 15 h. The title compound in the form of solid was filtered, washed with water and ethanol, and dried to prepare 15.7 g of the title compound (Yield: 84.4%).

$^1$H NMR (δ, CDCl$_3$): 8.86 (m, 2H), 8.55 (s, 1H), 7.82 (m, 3H), 7.73 (m, 1H), 7.40 (m, 3H), 4.60 (m, 2H), 4.24 (m, 2H), 4.08 (m, 1H), 3.99 (m, 1H), 3.95 (s, 3H), 3.45 (m, 2H), 1.13 (m, 2H), 0.89 (m, 2H) Mass (FAB): 528 (M+H)

Example 7

Preparation of methanesulfonic acid salt of 7-(aminomethyl-4-methoxyimino-1-pyrrolidinyl)-1-cyclopropyl-6-fluoro-1,4-dihydro-4-oxo-1,8-naphthyridine-3-carboxylic acid

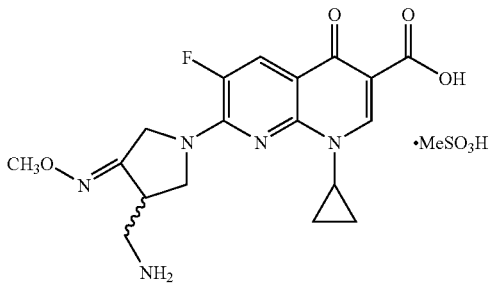

Water (60 ml), the compound (30.0 g) synthesized in Example 1 and isopropanol (210 ml) were in turn introduced into a reaction vessel, and heated to 40~45° C. Methanesulfonic acid (6.22 g) was dropwise added to the reaction mixture. After stirring the reaction mixture for about 0.5 h at a temperature of 40~45° C., it was cooled to 27~35° C. The compound (1)(0.03 g) was added to the reaction mixture. The reaction mixture was slowly cooled to room temperature and stirred for about 17 h to precipitate the title compound in the form of solid. The reaction mixture in the form of dispersion solution was cooled to −1~1° C., stirred for about 3 h, filtered, washed with isopropanol, dried and absorbed to prepare 29.0 g of the title compound (Yield: 95.1%).

$^1$H NMR (δ, DMSO-$d_6$): 8.59 (s, 1H), 8.06 (d, J=12.4 Hz, 1H), 4.58 (bs, 2H), 4.37 (m, 1H), 3.90 (s, 3H), 3.83 (bs, 1H), 3.71 (m, 1H), 3.40 (m, 1H), 3.24~3.10 (m, 2H), 2.32 (s, 3H), 1.20~1.05 (m, 2H), 1.03~1.02 (m, 2H) Mass (FAB): 486 (M+H)

Example 8

Preparation of methanesulfonic acid salt of 7-(aminomethyl-4-methoxyimino-1-pyrrolidinyl)-1-cyclopropyl-6-fluoro-1,4-dihydro-4-oxo-1,8-naphthyridine-3-carboxylic acid

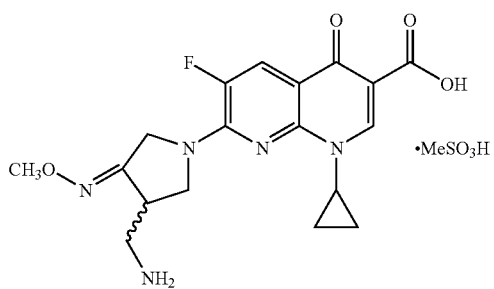

The title compound was prepared in yield of 91.7% in accordance with the procedure as described in Example 7, except that THF (240 ml) was used instead of isopropanol (210 ml), and methansulfonic acid was used in the amount of 6.04 g instead of 6.22 g.

INDUSTRIAL AVAILABILITY

If the novel synthesis process of two steps according to the present invention is used, the improved effect such as simplicity of the preparation process, increase of yield, improvement of productivity, decrease of manufacturing costs and the like can be achieved by reducing conventional three-step synthesis process to two-step process.

What is claimed is:
1. A process for preparing acid salts of Gemifloxacin represented by formula 1, which comprises the steps of
   a) adding a compound of formula 5 to naphthyridine carboxylic acid of formula 2 and 3-aminomethyl-4-methoxyiminopyrrolidine salt of formula 3 in water, an organic solvent or a mixed solvent thereof in the presence of an organic base to carry out a coupling reaction, and
   b) adding an acid of formula HA to the resulting compound of formula 4 in water, an organic solvent or a mixed solvent thereof to carry out deprotection and salt formation reactions at the same time:

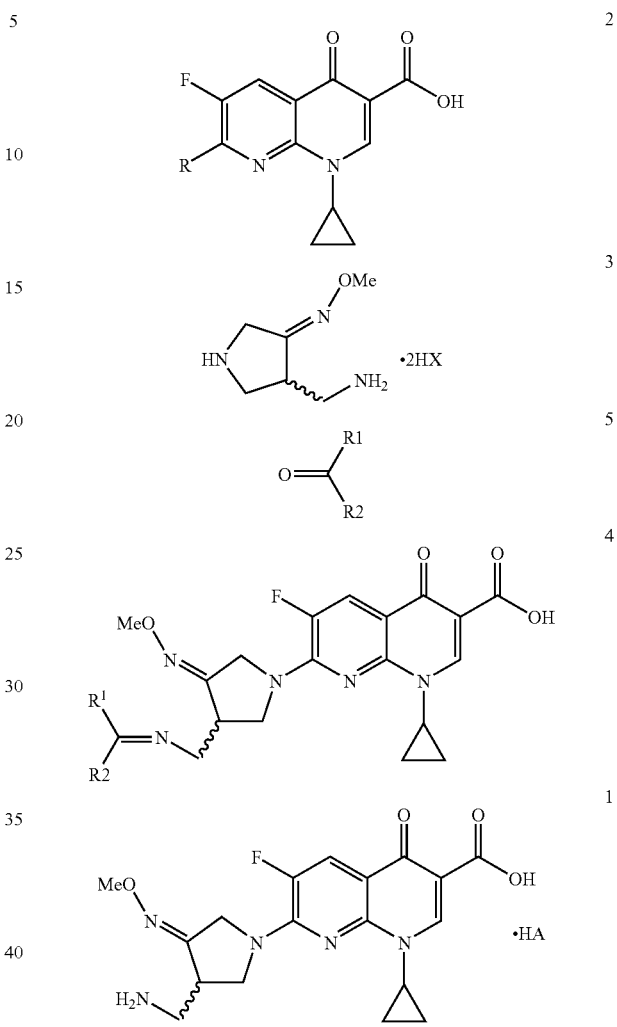

wherein,
R represents Cl, F, Br, I, methanesulfonyl or paratoluenesulfonyl,
Me represents methyl,
HX represents hydrochloric acid, hydrobromic acid, hydroiodic acid, trifluoroacetic acid, methanesulfonic acid, paratoluenesulfonic acid, or sulfuric acid,
R1 and R2 independently of each other represent hydrogen, a straight or branched, saturated or unsaturated $C_1$~$C_6$ alkyl group, a saturated or unsaturated $C_3$~$C_6$ cycloalkyl group, or an aromatic group which is unsubstituted or substituted by $C_1$~$C_6$ alkyl, $C_1$~$C_6$ alkoxy, hydroxy, cyano or halogen, or
R1 and R2 together with a carbonyl group to which they are bonded form a ring, and
HA is an organic acid or an inorganic acid.
2. The process of claim 1, wherein step a), step b) or both steps a) and b) are carried out in a mixed solvent of an organic solvent with water.
3. The process of claim 1, wherein the compound of formula 5 is selected from the group consisting of benzaldehyde, 2-chlorobenzaldehyde, 2-hydroxybenzaldehyde, 4-methoxybenzaldehyde and 1-naphthaldehyde.

4. The process of claim 2, wherein the organic solvent of step a) is acetonitrile, and that of step b) is isopropanol or tetrahydrofuran (THF).

5. The process of claim 1, wherein the organic base is selected from the group consisting of triethylamine, trimethylamine, diisopropylethylamine, 1,8-diazabicyclo [5.4.0] undec-7-ene, and 1,5-diazabicyclo[4.3.0]non-5-one.

6. The process of claim 1, wherein the compound of formula 5 is used in an amount of 1 to 3 times to that of the compound of formula 2.

7. The process of claim 1, wherein the organic base of step a) is used in an amount of 3 to 4 times to that of the compound of formula 2, and the reaction is carried out at a reaction temperature of 0 to 30° C.

8. The process of claim 7, wherein the organic base is triethylamine.

9. The process of claim 1, wherein the acid of formula HA is used in an amount of 80 mol % to 120 mol % relative to the compound of formula 4, the temperature on adding the acid is in the range of 40~50° C., and the temperature after adding the acid is in the range of 0~20° C.

10. The process of any one of claims 1-9, wherein the acid of formula HA is methanesulfonic acid.

11. A compound represented by the following formula 4:

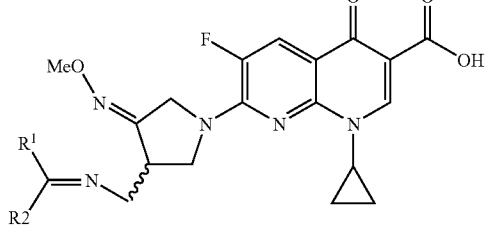

wherein,

Me represents methyl, $R^1$ and $R^2$ independently of each other represent hydrogen, a straight or branched, saturated or unsaturated $C_1$~$C_6$ alkyl group, a saturated or unsaturated $C_3$~$C_6$ cycloalkyl group, or an aromatic group which is unsubstituted or substituted by $C_1$~$C_6$ alkyl, $C_1$~$C_6$ alkoxy, hydroxy, cyano or halogen, or $R^1$ and $R^2$ together with a carbonyl group to which they are bonded form a ring.

12. The process of claim 1, wherein a separate recrystallization step is not performed.

13. The process of claim 1, wherein an acid salt of Gemifloxacin is formed in a yield of 90% or more.

14. The process of claim 1, wherein said acid salts of Gemifloxacin represented by formula 1 prepared according to the process contain 0.1% or less of a compound of formula 8 as an impurity:

* * * * *